United States Patent
Schmitt

(10) Patent No.: US 9,338,583 B2
(45) Date of Patent: May 10, 2016

(54) METHOD FOR ENERGY EFFICIENT BODY SENSOR NETWORK DISCOVERY

(75) Inventor: Ruediger Schmitt, Maplewood, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 13/810,908

(22) PCT Filed: Jul. 14, 2011

(86) PCT No.: PCT/IB2011/053149
§ 371 (c)(1),
(2), (4) Date: Jan. 18, 2013

(87) PCT Pub. No.: WO2012/011031
PCT Pub. Date: Jan. 26, 2012

(65) Prior Publication Data
US 2013/0115885 A1 May 9, 2013

Related U.S. Application Data

(60) Provisional application No. 61/367,028, filed on Jul. 23, 2010.

(51) Int. Cl.
*H04W 16/14* (2009.01)
*H04W 4/00* (2009.01)
(Continued)

(52) U.S. Cl.
CPC ............ *H04W 4/008* (2013.01); *A61B 5/0002* (2013.01); *A61B 5/0022* (2013.01);
(Continued)

(58) Field of Classification Search
CPC ................................. H04L 67/12; H04W 4/20
See application file for complete search history.

(56) References Cited

U.S. PATENT DOCUMENTS

2004/0058717 A1* 3/2004 McDonnell et al. .......... 455/567
2005/0090242 A1* 4/2005 Kotzin et al. ............. 455/422.1
(Continued)

FOREIGN PATENT DOCUMENTS

WO 2004109992 A1 12/2004
WO 2005062232 A2 7/2005
(Continued)

OTHER PUBLICATIONS

Ke, C-Y., et al.; EcoPlex: Empowering Compact Wireless Sensor Platforms via Roaming and Interoperability Support; 2009; The Sixth Annual International Conference on Mobile and Ubiquitous Systems: Computing, Networking, and Services (MobiQuitous) 9 pages.
(Continued)

*Primary Examiner* — Cindy Trandai

(57) ABSTRACT

When monitoring a patient in a healthcare environment, a location of a battery-powered mobile aggregator (MA) sensor (22), which is mounted on a patient with one or more other patient-mounted sensors (12, S1, S2, S3), is monitored. The MA (22) maintains a personal area network (PAN) (24) for the sensors (12, S1, S2, S3) and wirelessly transmits signals from patient mounted sensors (12, S1, S2, S3) to a wired network (18). When the MA (22) comes within range of a mains-powered fixed aggregator (FA) (16), the MA (22) is informed of the availability of the FA (16), transfers patient data communication duties to the FA (16), and shuts down its PAN to conserve battery power. If the patient moves out of range of the FA (16), then the MA (22) regenerates the PAN (24) and resumes wireless patient data transmission.

20 Claims, 5 Drawing Sheets

(51) Int. Cl.

| | | |
|---|---|---|
| *A61B 5/00* | (2006.01) | |
| *G06F 19/00* | (2011.01) | |
| *H04W 48/16* | (2009.01) | |
| A61B 5/0205 | (2006.01) | |
| A61B 5/11 | (2006.01) | |
| H04W 84/00 | (2009.01) | |
| H04W 84/22 | (2009.01) | |

(52) U.S. Cl.
CPC ......... *A61B 5/0024* (2013.01); *G06F 19/3418* (2013.01); *H04W 48/16* (2013.01); *A61B 5/0205* (2013.01); *A61B 5/1112* (2013.01); *A61B 2560/0209* (2013.01); *H04W 84/005* (2013.01); *H04W 84/22* (2013.01); *Y02B 60/50* (2013.01)

(56) References Cited

U.S. PATENT DOCUMENTS

| | | | |
|---|---|---|---|
| 2006/0281553 A1* | 12/2006 | Hawkins et al. | 463/42 |
| 2008/0107072 A1* | 5/2008 | Viorel et al. | 370/329 |
| 2008/0164997 A1* | 7/2008 | Aritsuka et al. | 340/539.13 |
| 2008/0228045 A1 | 9/2008 | Gao et al. | |
| 2010/0062711 A1* | 3/2010 | Park | 455/41.2 |
| 2010/0128636 A1 | 5/2010 | Seeling et al. | |
| 2010/0176941 A1* | 7/2010 | Jain et al. | 340/539.13 |
| 2010/0315225 A1* | 12/2010 | Teague | 340/539.12 |
| 2011/0130092 A1* | 6/2011 | Yun et al. | 455/39 |
| 2012/0185569 A1* | 7/2012 | Das et al. | 709/219 |

FOREIGN PATENT DOCUMENTS

| | | |
|---|---|---|
| WO | 2006050206 A1 | 5/2006 |
| WO | 2009090575 A1 | 7/2009 |

OTHER PUBLICATIONS

Park, J-T., et al.; Context-Aware Handover with Power Efficiency for u-Healthcare Service in WLAN; 2009; International Conference on New Trends in Information and Service Science; pp. 1279-1283.

Zhang, Z., et al.; Design and implementation of a novel MAC layer handoff protocol for IEEE 802.11 wireless networks; 2009; IEEE International Symposium on Parallel & Distributed Processing; pp. 1-5.

* cited by examiner

METHOD FOR ENERGY EFFICIENT BODY SENSOR NETWORK DISCOVERY

CROSS REFERENCE TO RELATED APPLICATIONS

This application is a national filing of PCT application Serial No. PCT/IB2011/053149, filed Jul. 14, 2011, published as WO 2012/011031 A1 on Jan. 26, 2012, which claims the benefit of U.S. provisional application Ser. No. 61/367, 028 filed Jul. 23, 2010, which is incorporated herein by reference.

The present innovation finds application in patient monitoring systems, particularly with regard to physiological monitoring systems. However, it will be appreciated that the described techniques may also find application in other monitoring systems, other healthcare information collection scenarios, other status monitoring techniques, and the like.

Recent advances in semiconductor and circuit miniaturization, bio sensor development, and wireless communication have made small integrated sensors with on-board processing and wireless data transfer a reality. These sensors use short range wireless communication protocols and can be combined into wearable wireless sensor networks to acquire data concerning the physiological parameters (heart rate, oxygen saturation, blood pressure, temperature, electro-cardiogram (ECG), etc.) as well as the physical activities of a person. The applications for these sensor networks include home monitoring of the elderly, monitoring of patients with chronic disease, wellness, rehabilitation and patient monitoring in hospitals. For example, a patient may have several wireless bio-sensor nodes attached to the body, and sensor data is wirelessly transmitted to a wireless gateway and further sent over a wired network to a server for processing, visualization and storage. The server may be located in a hospital in case of patient monitoring.

Since the body sensors are battery powered, low-power consumption for all system components, including wireless data transmission, is a crucial performance parameter. Therefore, low-power short-range radio technologies are useful for wireless connectivity in the described systems and methods. One wireless technology that has gained the traction in the healthcare industry for this application due to its low power consumption, low complexity, and low cost, is the wireless personal area network (WPAN) technology defined in the IEEE 802.15.4 standard. An IEEE 802.15.4 WPAN comprises one WPAN coordinator and one or more end devices. A number of physical channels have been defined, i.e. 10 in the 2.4 GHz ISM band. A WPAN usually operates in one frequency chosen by the PAN coordinator in a way to minimize interference from other IEEE 802.14.5 WPANs or non-802.15.4 traffic.

Two types of network nodes have been defined in the standard: full function devices (FFD) and reduced function devices (RFD). RFDs implement a subset of 802.15.4 primitives and cannot function as WPAN coordinators. RFD radios are turned off as much as possible to minimize power consumption. FFDs have a full implementation of the primitives defined in the standard and are able to function as PAN coordinators. Although IEEE 802.15.4 defines an optional synchronized channel access mechanism using beacons that allows for bandwidth reservations as well as for the WPAN coordinator to enter sleep mode, the vast majority of WPAN implementations do not use it. To reduce power consumption the radios are turned off as much as possible. Generally, the PAN coordinator has to be on at all times to receive transmissions from the end devices.

Current state of the art mechanisms put the burden of rediscovering a fixed aggregator (FA) on the mobile wireless personal area network (WPAN) devices, thus increasing their power consumption and reducing their battery life. In the simplest case, the sensors or WPAN end devices individually scan for the fixed aggregator patient area network (PAN) and report findings to a mobile aggregator (MA) to allow the MA to abandon its PAN. The MA itself cannot scan on channels other than the one the MA is operating on, since the MA has to be able to receive asynchronous transmissions from the end devices. In a more efficient mechanism, the MA instructs the end devices, one at a time, to perform a scan and report the results to the MA. Even in the latter approach power is consumed by the end devices for scanning and by both the end devices and the MA for signaling. More specifically, if each of the nodes or sensors sends out a beacon request or listens for transmissions from a bedside monitor or other fixed aggregator unit, the nodes or individual monitors will have shortened battery life.

The present application provides new and improved systems and methods for permitting one or more mobile devices in a mobile WPAN to discover their fixed aggregator while minimizing the power consumption of the battery-powered mobile WPAN devices, which overcome the above-referenced problems and others.

In accordance with one aspect, a method of transferring a patient monitoring sensor group between fixed and mobile modes of communication with a wired healthcare network comprises detecting the sensor group, which comprises one or more patient-mounted sensors and a mobile aggregator sensor, within range of a fixed aggregator module. The method further comprises informing the mobile aggregator sensor that it and the one or more patient-mounted sensors are within range of the fixed aggregator module, and, when the fixed aggregator module is within range, communicating status information from the sensor group (52) to a wired network via the fixed aggregator module.

In accordance with another aspect, a system that facilitates transferring a patient monitoring sensor group between fixed and mobile modes of communication with a wired healthcare network comprises a fixed aggregator module that detects the sensor group, which includes one or more patient-mounted sensors and a mobile aggregator sensor, when the sensor group is within range of the fixed aggregator module. The fixed aggregator notifies the mobile aggregator sensor that the sensor group is within range of the fixed aggregator module. The one or more patient-mounted sensors communicate patient status information to a wired network via the fixed aggregator module when the sensor group is notified that it is within range of the fixed aggregator module and to the wired network via a mobile aggregator module when the sensor group is not within range of the fixed aggregator module.

In accordance with another aspect, a method of transferring a patient monitoring device between fixed and mobile modes of communication with a wired healthcare network comprises monitoring a location of a mobile sensor group comprising one or more patient-mounted sensors and a mobile aggregator sensor that maintains a mobile aggregator personal area network (MA-PAN) via which sensed patient information is relayed from the sensors to a wired network. The method further comprises informing the mobile aggregator sensor that it and the one or more patient-mounted sensors are within range of a mains-powered fixed aggregator module, and instructing the one or more patient-mounted sensors to communicate patient status information to the wired network via a fixed aggregator personal area network (FA-PAN) when the sensor group is within range of the fixed aggregator module. Additionally, the method comprises terminating the MA-PAN when the sensor group is within range of the fixed aggregator module in order to conserve battery power at the mobile aggregator sensor.

One advantage is that battery power is conserved.

Another advantage resides in providing continuous patient monitoring as a patient moves about a monitoring area.

Still further advantages of the subject innovation will be appreciated by those of ordinary skill in the art upon reading and understanding the following detailed description.

The drawings are only for purposes of illustrating various aspects and are not to be construed as limiting.

To overcome the aforementioned problems, the described systems and methods facilitate conserving battery life by handing off the mobile patient sensors between the mobile and fixed networks, and placing the burden of determining whether the patient-carried personal area network (PAN) is in the vicinity of the fixed aggregator on the bedside monitor, which uses wall power and therefore has no battery life issues.

Figure 1:
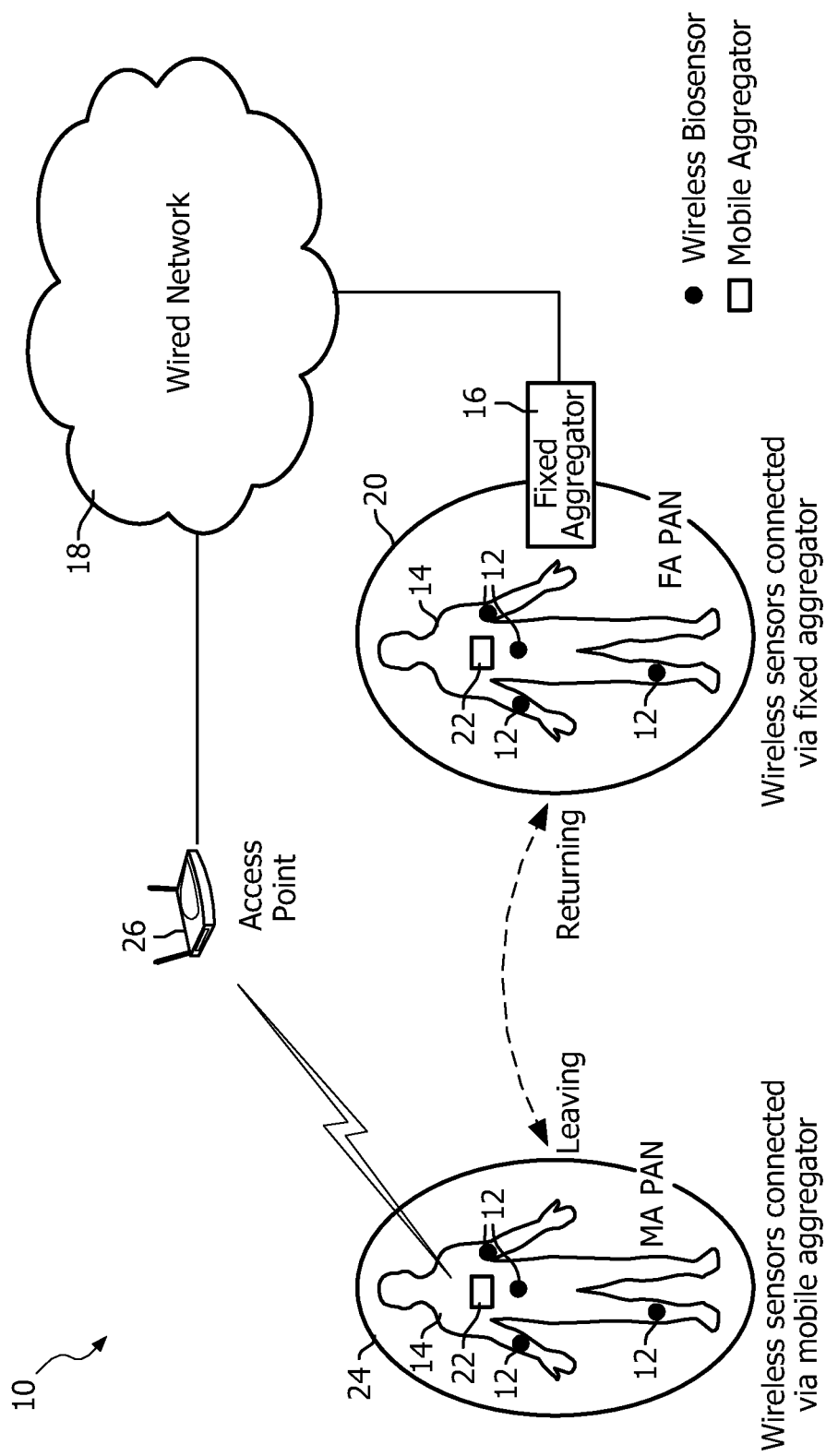
FIG. 1 illustrates a system that facilitates mobile connectivity using two connectivity modes for a plurality of on-body wireless sensors positioned on a patient.

FIG. 1 illustrates a system 10 that facilitates mobile connectivity using two connectivity modes for a plurality of on-body wireless sensors 12 positioned on a patient 14. In the first mode, shown on the right and henceforth called fixed mode (FM), all on-body sensors connect to a fixed aggregator (FA) 16, which receives the sensor data and transmits it over the wired network 18 (e.g., a hospital or healthcare environment network). The FA is mains powered and acts as the PAN coordinator for the FA-PAN 20. In addition to serving as the point of attachment to the wired network for the mobile sensors, the FA can process the data. In the second operating mode, shown on the left in FIG. 1 and henceforth called mobile mode (MM), the monitored person has left the service area of the fixed aggregator. Consequently, an on-body mobile aggregator (MA) 22 creates a second PAN, MA-PAN 24, to which the sensors connect. The mobile aggregator receives the sensor data and forwards it through a second, local area wireless link such as IEEE 802.11 (Wireless LAN) via an access point 26 to the wired network. The mobile aggregator can be a stand-alone device. In one embodiment, the MA 22 is one of the body sensors and contains additional functionality for carrying out the reception and forwarding of sensor data. When the monitored patient re-enters the service area of the fixed aggregator, the on-body sensors 12 switch back to the first operating mode, i.e. they re-connect to the fixed FA-PAN 20. The mobile aggregator then abandons its MA-PAN 24. During mobile mode, the mobile aggregator's power consumption may increase in order to receive the sensor data on the short range radio at all times, and transmit it through the local area network radio.

In one embodiment, the FA 16 is part of a bedside monitor (not shown) that detects communications between the mobile aggregator and the nodes or sensors and determines that the patient carried PAN is within range based on signal strength. In another embodiment, the fixed and mobile units are both connected to the WLAN and can use the WLAN network to monitor proximity. In another embodiment, the mobile aggregator receives PAN beacon requests from the fixed unit to establish a communication link which establishes proximity. In another embodiment, the bedside monitor can include a second short range radio unit which either scans for signals from the individual on body sensor nodes or sends beacon signals to the mobile aggregator to establish proximity.

In another embodiment, radio signal strength is relied upon to determine proximity of the wireless sensors to the fixed aggregator. However, a map and an asset tracking system or GPS systems can be utilized to determine proximity at the server level.

Figure 2:
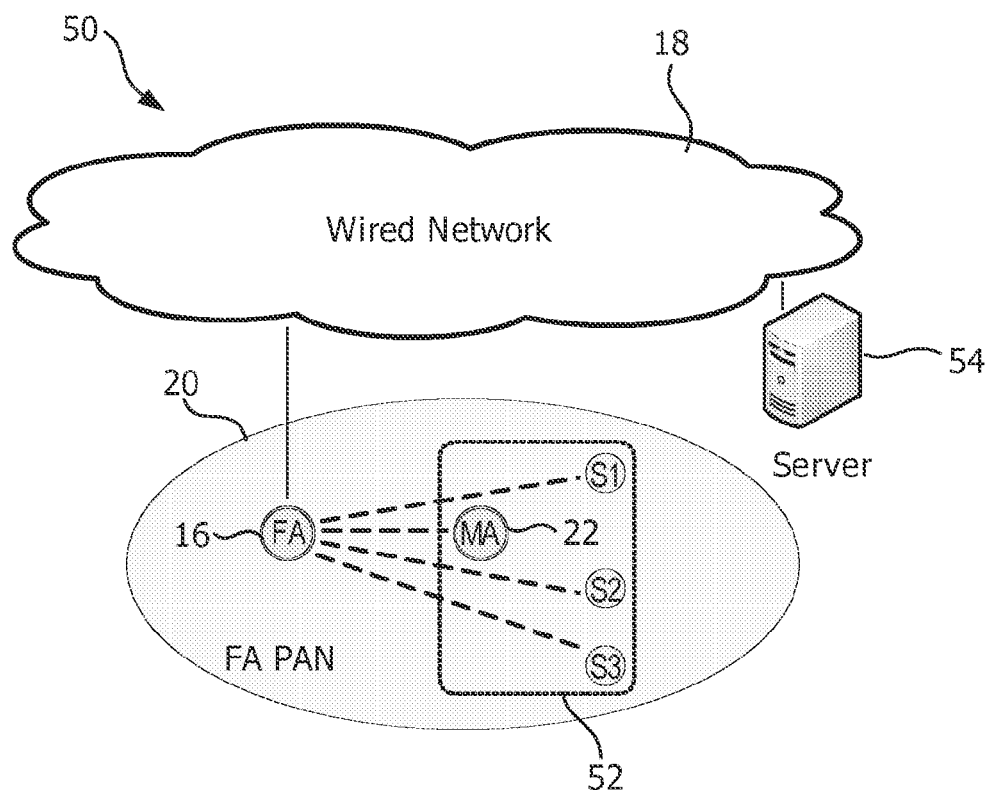
FIG. 2 illustrates a system that facilitates conserving battery power in on-body devices or sensors.

FIG. 2 illustrates a system 50 that facilitates conserving battery power in on-body devices or sensors. The fixed aggregator 16 discovers that the mobile PAN has returned to the FA's vicinity and that connectivity between the FA and the mobile group of sensors 52 is once again possible using short range radio. This approach improves battery life of the mobile sensors S1, S2, S3, and therefore increases convenience for the user (e.g., layman, medical provider, etc.). In one embodiment, the FA only connects to sensors that are part of a mobile sensor group connected to the FA-PAN 20. Thus, FIG. 2 shows an example configuration for fixed mode operation where the FA 16 is the PAN coordinator for the FA-PAN. Three reduced function device (RFD) sensors S1, S2, and S3, as well as a fourth sensor (the MA) 22, which is a full-function device and WLAN-capable, are connected to the FA-PAN. The MA's WLAN radio (not shown) is not used for communication and turned off to save power in this embodiment. All data coming from the sensors is routed through the FA to the wired network 18 and on to a server 54. As the mobile sensor group 52 moves away from the FA 16, communication with the FA is no longer possible, and the communication scheme transitions from that shown in FIG. 2 to that shown in FIG. 3.

Figure 3:
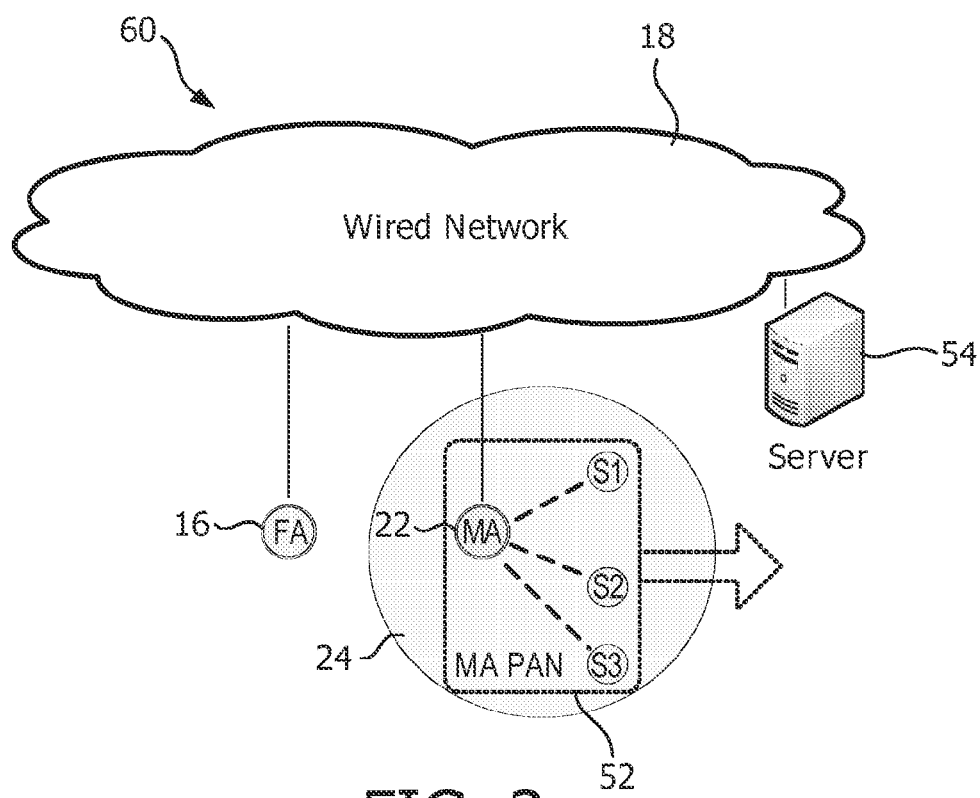
FIG. 3 illustrates a system in a mobile mode of operation, where the MA sensor has started its own PAN (MA-PAN) and the sensors have connected to the MA PAN and the MA further transmits the patient information to the wired network.

FIG. 3 illustrates a system 60 in a mobile mode of operation, where the MA sensor 22 has started its own PAN (MA-PAN) 24 and the sensors S1, S2 and S3 have connected to the MA-PAN and the MA further transmits the patient information to the wired network. The MA has established a connection to the WLAN infrastructure and uses this link to forward the sensor data to the wired network 18. The FA 16 does not have any more devices attached to it after the mobile sensor group 52 has left, which frees up its short range radio. In this embodiment, the FA uses its short range radio to scan for the MA-PAN 24 for transmissions from the MA 22 in all channels (passive scan) or by sending beacon requests (active scan) in all channels. The MA may also store its current channel in the server 54 via the wired network, from which the FA can retrieve its current channel for a more targeted scanning. The MA can be notified that the mobile sensor group is once again in the vicinity of the FA in several ways. In one embodiment, the FA communicates with the MA over short range radio link. In another embodiment, the FA communicates with the MA through the wired network over a WLAN link. In another embodiment, the MA detects beacon requests from the FA.

Figure 4:
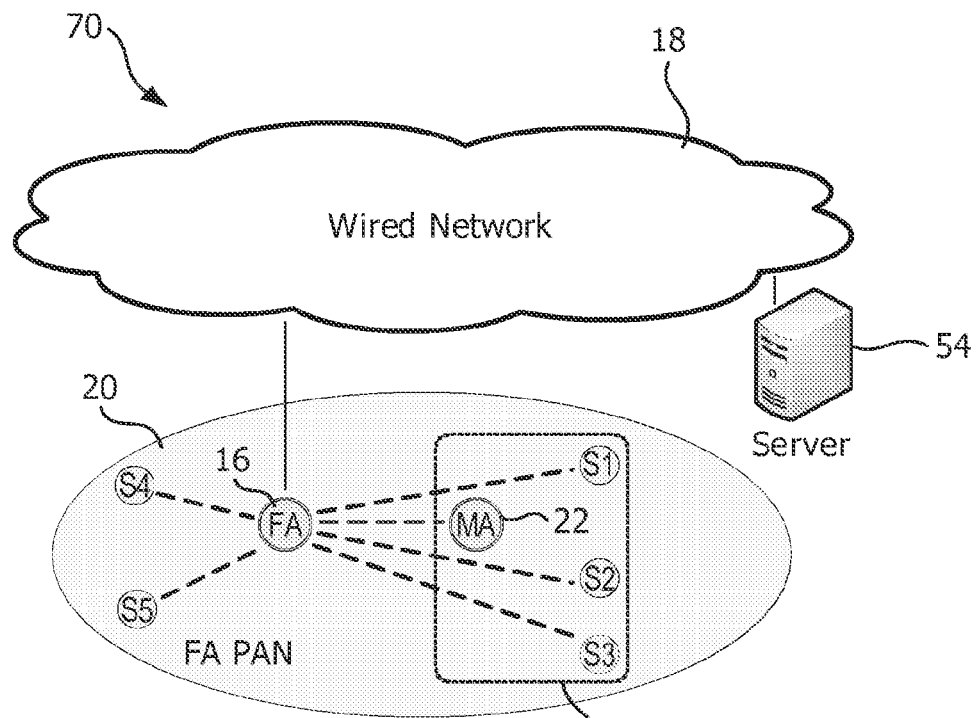
FIG. 4 illustrates a system in which the FA has fixed sensors connected to its PAN, wherein the sensors are not part of the mobile sensor group.

FIG. 4 illustrates a system 70 in which the FA 16 has fixed sensors S4, S5 connected to its PAN 20, wherein the sensors S4, S5 are not part of the mobile sensor group 52. As the mobile sensor group leaves the coverage area of the FA and starts its own PAN, S4 and S5 remain connected to the FA. In this case the FA cannot easily change its channel to scan for the MA 22 because it has to maintain connectivity to the fixed sensors S4 and S5. In this embodiment, the FA uses a second on-board short range radio (not shown) to scan for the MA-PAN for transmissions from the MA. The scanning can be either passive or active as described previously. The MA can be notified that short range radio connectivity can be re-established with the FA through the mechanisms described with regard to FIG. 3.

In another embodiment, the FA instructs one of the fixed sensors connected to it, e.g. S4 or S5, to scan for the MA-PAN. The scanning can be either passive or active as described previously with regard to FIG. 3. The fixed sensor reports the results back to the FA. The MA can be notified that short range radio connectivity can be re-established with the FA through the mechanisms described with regard to FIG. 3.

Figure 5:
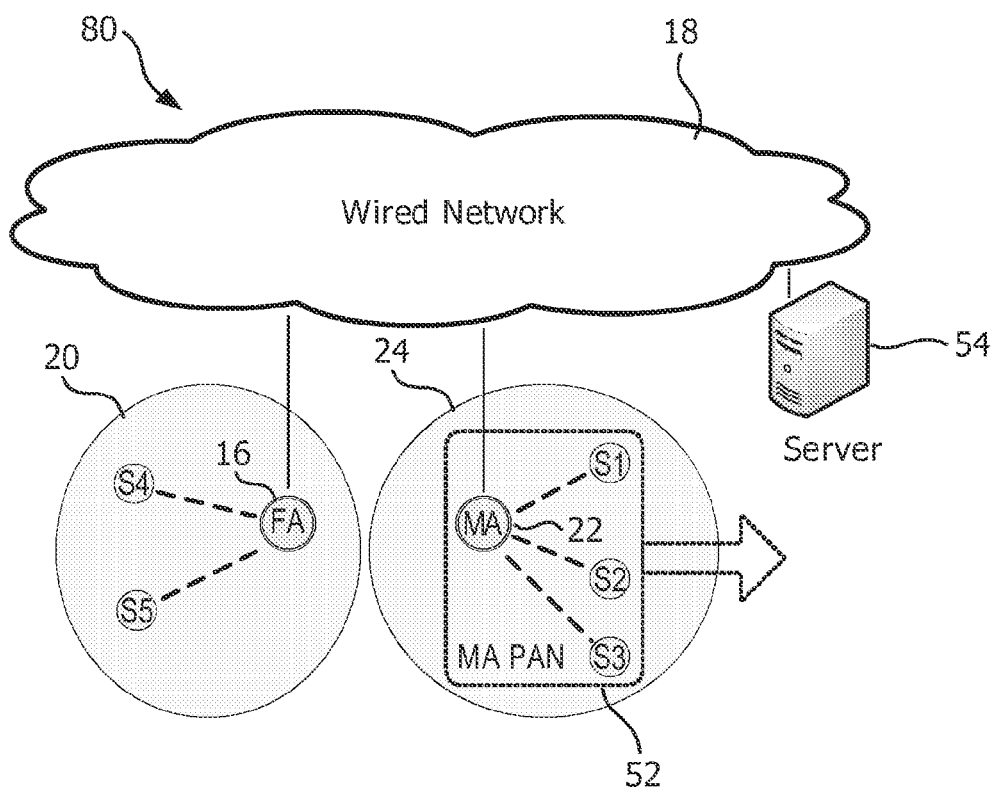
FIG. 5 illustrates a system in a mobile mode of operation, where the MA sensor has started its own PAN (MA-PAN) and the sensors have connected to the MA PAN and the MA further transmits the patient information to the wired network. The FA continues to have fixed sensors connected to its PAN.

FIG. 5 illustrates a system in a mobile mode of operation, where the MA sensor has started its own PAN (MA-PAN) and the sensors have connected to the MA PAN and the MA further transmits the patient information to the wired network. The FA continues to have fixed sensors connected to its PAN. The MA may store information about its WLAN connectivity (WLAN channel, etc.) on a server 54 in the network 18, where the FA can retrieve it for a more targeted scanning. To infer from successful receptions of WLAN transmissions from the MA that the MA is in range of the short range radio, the FA may compare the received signal strength (RSS) of the WLAN transmission to a pre-determined threshold. If the RSS exceeds the pre-determined threshold, short range radio communication may be determined to be possible. The MA can be notified that short range radio connectivity can be re-established with the FA through the mechanisms described with regard to FIG. 3.

Figure 6:
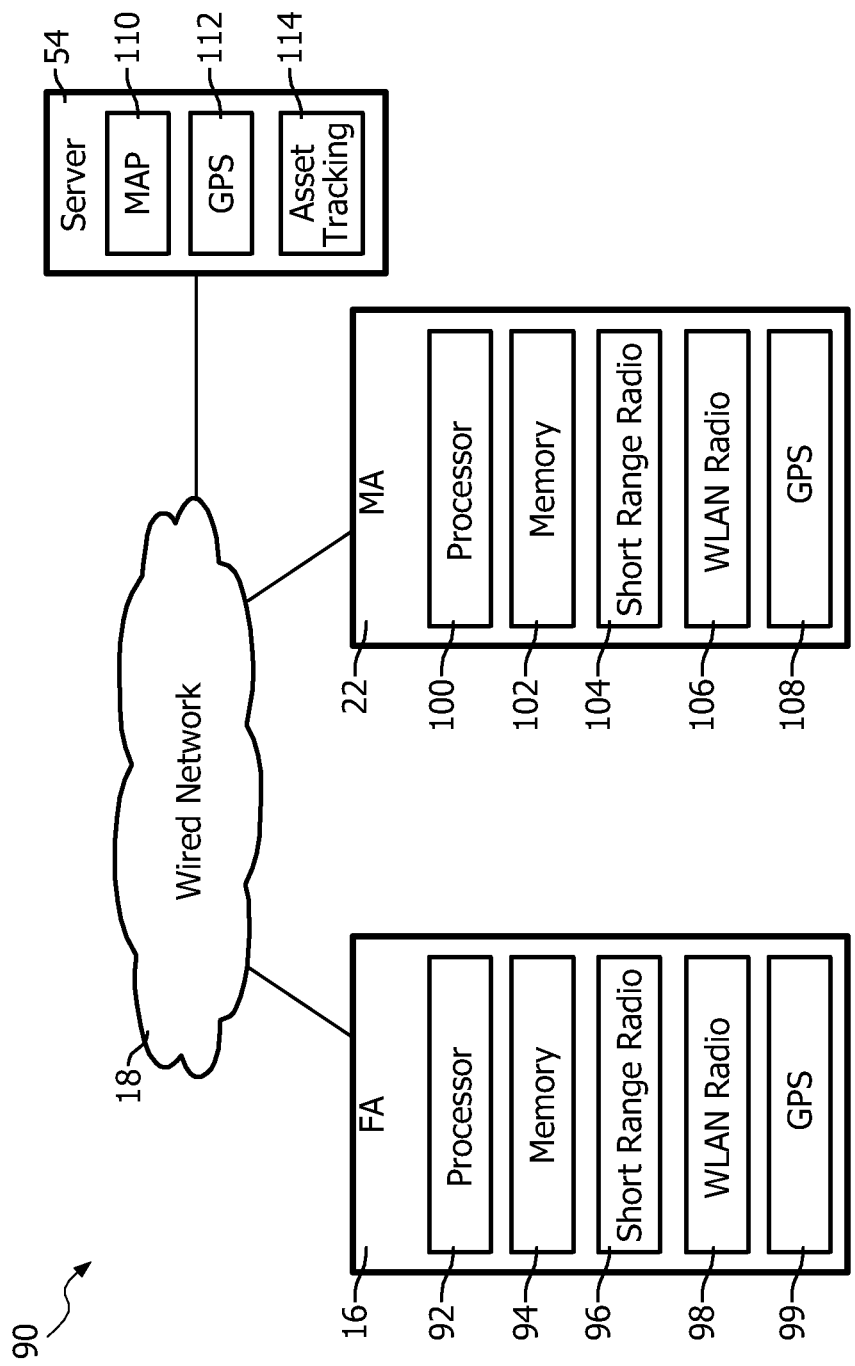
FIG. 6 illustrates a system showing the FA and MA in greater detail, and coupled to the wired network, e.g., via a wired or wireless connection.

FIG. 6 illustrates a system 90 showing the FA 16 and MA 22 in greater detail, and coupled to the wired network 18, e.g., via a wired or wireless connection. It will be appreciated that each of devices (e.g., the fixed aggregator, the mobile aggregator, the server etc.), and the wired network described in various embodiments and figures herein may include a memory or computer-readable medium that stores, and one or more processors that executes, computer-executable instructions for performing the various functions, actions, steps, methods, etc., described herein. For instance, the FA 16 includes a processor 92 and memory 94, and the MA 22 includes a processor 100 and a memory 102. The memory may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

A server 54 is coupled to the wired network includes one or more maps 110 of a healthcare facility or environment (e.g., a hospital, nursing home, a patient's home in the case of home-monitoring, etc.). Additionally, each of the FA, the MA, and a server 54 coupled to the wired network includes a GPS module 99, 108, 112 respectively with which the location of the MA relative to the FA can be tracked. In another embodiment, the server includes an asset tracking system 114 that is used in conjunction with the map(s) 110 to track the location of the MA relative to the FA.

The system 90 facilitates transferring a patient monitoring sensor group (FIGS. 2-5) between fixed and mobile modes of communication with the wired network 18. In one embodiment, the fixed aggregator module detects when the sensor group and/or the MA 22 is within a predefined distance from the fixed aggregator module (e.g., 10 meters or so). When the MA is determined to be within range of the FA, The FA notifies the MA that the sensor group and the one or more patient-mounted sensors that are communicating through the MA switch over to communicate patient status information to the wired network 18 via the FA.

Several manners of detecting the MA are described herein. In one embodiment, the FA includes a short range radio 96 that scans a plurality of short range radio channels to detect transmissions from a short range radio 104 in the MA, in order to detect the sensor group. Additionally or alternatively, the FA includes a WLAN radio 98 that scans a plurality of WLAN radio channels to detect transmissions from a WLAN radio 106 in the MA, which the MA uses to transmit patient information received from the sensors to the wired network.

In another embodiment, the FA's processor 92 establishes a communication link with the wired network, and the MA's processor 100 also establishes a communication link with the wired network 18. The server 54 monitors the location of the mobile aggregator sensor relative to the fixed aggregator module using the map 112 and at least one of the GPS modules or the asset tracking system.

In another embodiment, the at least one of the short range radio 96 and the WLAN radio 98 transmits a beacon signal from the FA, and the MA includes at least one of a short range radio 104 and a WLAN radio 106 that transmits a signal indicating that the mobile aggregator sensor is within the predefined distance of the fixed aggregator module in response to the beacon signal.

The MA establishes a mobile aggregator personal area network (MA-PAN) when outside of the predefined distance from the fixed aggregator, receives patient parameter data from the one or more patient sensors via the MA-PAN, and transmits the patient parameter data to the wired network over a wireless local area network (WLAN) communication link. The patient parameter data may include without limitation information associated with a patient parameter including information associated with blood pressure, heart rate, respiratory rate, temperature, blood oxygen level, etc.

Figure 7:
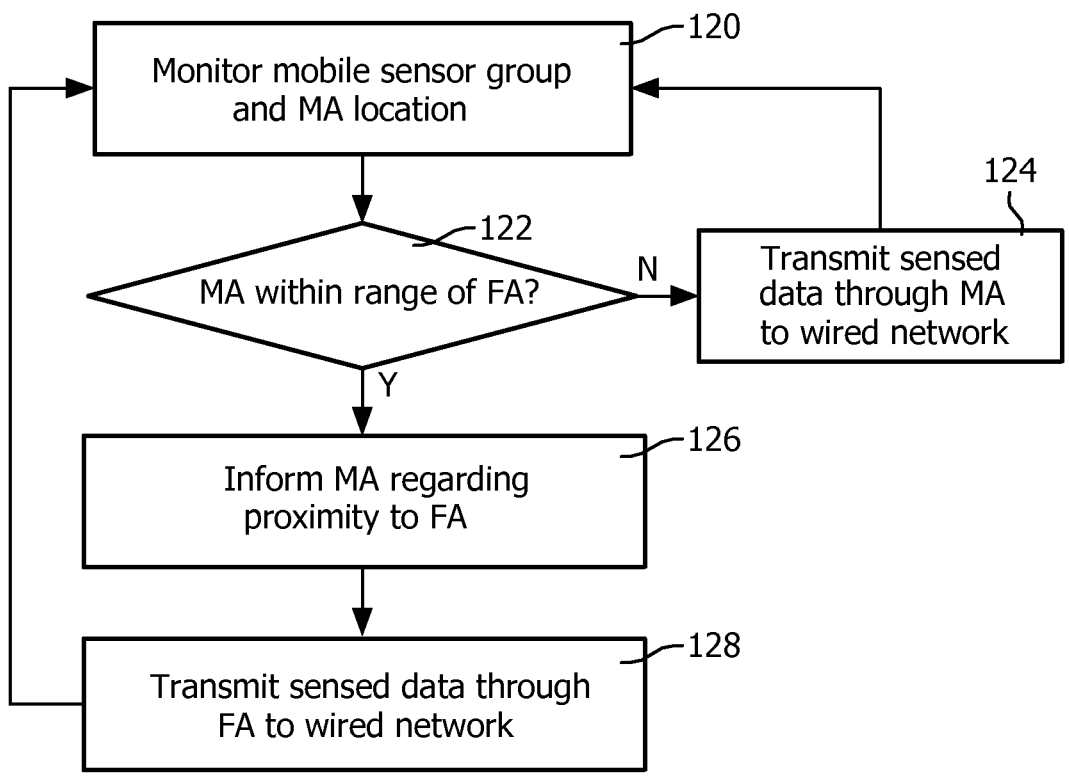
FIG. 7 illustrates a method of transferring a patient monitoring sensor group between fixed and mobile modes of communication with a wired healthcare network.

FIG. 7 illustrates a method of transferring a patient monitoring sensor group between fixed and mobile modes of communication with a wired healthcare network. At 120, a location of a patient-mounted, mobile sensor group is detected or monitored. The mobile sensor group comprises a plurality of reduced-function devices (RFDs) and at least one full-function device (FFD) that serves as a mobile aggregator (MA) sensor that aggregates information from all sensors in the group and transmits the information to a wired network. At 122, a determination is made regarding whether the MA is within range of the FA for communication. If not, then at 124, the sensed patient data is transmitted from the sensors through the MA to a wired network. If the MA is within range of the FA, then at 126 the MA is informed that it is within range of FA. At 128, the sensor group begins transmitting sensed information to the FA (e.g., using a short-range radio communication link or the like), which is mains-powered (e.g., plugged into a wall or the like). In this manner valuable battery power is conserved at the MA.

The MA and mobile sensor group location monitoring is performed periodically or continuously, so that if the MA moves out of range of the FA, then the sensor group reverts back to transmitting through the MA for communication of patient parameter data (e.g., blood pressure, heart rate, temperature, respiratory rate, blood-oxygen level, etc.) to the wired network (e.g., via a WLAN communication link or the like). Determining the location of the MA relative to the FA can be performed in various ways (e.g., GPS, asset tracking, beacon signal and response, etc.) as described with regard to the preceding figures.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A method of transferring a patient monitoring sensor group between fixed and mobile modes of communication with a wired healthcare network, comprising:
   detecting the sensor group, which comprises one or more patient-mounted sensors and a mobile aggregator sensor, within communication range of a fixed aggregator module;
   informing the mobile aggregator sensor that it and the one or more patient-mounted sensors are within range of the fixed aggregator module;
   when the fixed aggregator module is within range, communicating status information from the sensor group to a wired network via the fixed aggregator module while bypassing the mobile aggregator sensor; and
   terminating a mobile aggregator personal area network (MA-PAN), which is used for communication between the sensor group and the mobile aggregator sensor, when the sensor group is within range of the fixed aggregator module in order to conserve battery power at the mobile aggregator sensor.

2. The method according to claim 1, further including, when the mobile aggregator sensor is out of range of the fixed aggregator module:
   establishing the mobile aggregator personal area network (MA-PAN) at the mobile aggregator sensor when the mobile aggregator sensor is out of range of the fixed aggregator;
   receiving the status information from the one or more patient sensors at the mobile aggregator sensor via the MA-PAN; and
   transmitting the status information from the mobile aggregator sensor to the wired network and bypassing the fixed aggregator module.

3. The method according to claim 2, wherein the mobile aggregator sensor transmits the status information to the wired network over a wireless local area network (WLAN) communication link.

4. The method according to claim 1, wherein detecting the sensor group includes:
   monitoring, at the fixed aggregator module, a plurality of wireless local access network (WLAN) radio channels in order to detect WLAN transmissions from the mobile aggregator sensor.

5. The method according to claim 1, wherein detecting the sensor group includes:
   establishing a communication link between the wired network and each of the mobile aggregator sensor and the fixed aggregator module; and
   monitoring, at the wired network, a location of the mobile aggregator sensor relative to the fixed aggregator module using at least one of:
   a global positioning system (GPS) and a map of the of the healthcare facility; and
   a map of the healthcare facility and an asset tracking system.

6. The method according to claim 1, wherein detecting the sensor group includes:
   transmitting a beacon signal from the fixed aggregator module;
   receiving, via the wired network, location information from the mobile aggregator sensor indicating that the mobile aggregator sensor is within communication range of the fixed aggregator module.

7. The method according to claim 1, wherein detecting the sensor group includes:
   monitoring, at the fixed aggregator module, a plurality of short range radio channels in order to detect short range radio transmissions from the mobile aggregator sensor.

8. The method according to claim 1, wherein the status information includes information associated with a patient parameter including at least one of:
   blood pressure;
   heart rate;
   respiratory rate;
   temperature; and
   blood oxygen level.

9. The method according to claim 1, wherein the communication range is approximately 10 meters or less.

10. A non-transitory computer-readable medium carrying software for controlling a processor to configure and perform the method of claim 1.

11. A system that facilitates transferring a patient monitoring sensor group between fixed and mobile modes of communication with a wired healthcare network, comprising:
    a fixed aggregator module that detects the sensor group, which includes one or more patient-mounted sensors and a mobile aggregator sensor, when the sensor group is within range of the fixed aggregator module;
    wherein the fixed aggregator notifies the mobile aggregator sensor that the sensor group is within range of the fixed aggregator module; and
    wherein the one or more patient-mounted sensors communicate status information to a wired network via the fixed aggregator module, bypassing the mobile aggregator sensor, when the sensor group is notified that it is within range of the fixed aggregator module and to the wired network via a wireless network when the sensor group is not within range of the fixed aggregator module; and
    terminating a mobile aggregator personal area network (MA-PAN), which is used for communication between the sensor group and the mobile aggregator sensor, when the sensor group is within range of the fixed aggregator module in order to conserve battery power at the mobile aggregator sensor.

12. The system according to claim 11, wherein the mobile aggregator sensor:
- establishes the mobile aggregator personal area network (MA-PAN) when the mobile aggregator sensor is out of range of the fixed aggregator;
- receives the status information from the one or more patient sensors via the MA-PAN;
- transmits the status information to the wired network over a wireless local area network (WLAN) communication link.

13. The system according to claim 11, wherein the fixed aggregator module includes a WLAN radio that scans a plurality of WLAN radio channels to detect transmissions from a WLAN radio in the mobile aggregator sensor, in order to detect the sensor group.

14. The system according to claim 11, wherein the fixed aggregator module includes a processor that establishes a communication link with the wired network and the mobile aggregator sensor includes a processor that establishes a communication link with the wired network, and wherein a server coupled to the wired network monitors a location of the mobile aggregator sensor relative to the fixed aggregator module using at least one of:
- a global positioning system (GPS) and a map of the of the healthcare facility; and
- a map of the healthcare facility and an asset tracking system.

15. The system according to claim 11, wherein the fixed aggregator module includes at least one of a short range radio and a wireless local area network (WLAN) radio that transmits a beacon signal from the fixed aggregator module, and wherein the mobile aggregator sensor includes at least one of a short range radio and a wireless local area network (WLAN) radio that transmits indicating that the mobile aggregator sensor is within range of the fixed aggregator module in response to the beacon signal.

16. The system according to claim 11, wherein the fixed aggregator module includes a short range radio that scans a plurality of short range radio channels to detect transmissions from a short range radio in the mobile aggregator sensor, in order to detect the sensor group.

17. The system according to claim 11, wherein the status information includes information associated with a patient parameter including at least one of:
- blood pressure;
- heart rate;
- respiratory rate;
- temperature; and
- blood oxygen level.

18. The system according to claim 11, wherein the range of the fixed aggregator module is approximately 10 meters or less.

19. The system according to claim 11, wherein the fixed aggregator module resides on a patient bedside monitor.

20. A method of transferring a patient monitoring device between fixed and mobile modes of communication with a wired healthcare network, comprising:
- monitoring a location of a mobile sensor group comprising one or more patient-mounted sensors and a mobile aggregator sensor that maintains a mobile aggregator personal area network (MA-PAN) via which sensed patient information is relayed from the one or more patient-mounted sensors to a wired network;
- informing the mobile aggregator sensor that it and the one or more patient-mounted sensors are within range of a mains-powered fixed aggregator module;
- instructing the one or more patient-mounted sensors to communicate status information to the wired network via a fixed aggregator, while bypassing the mobile aggregator sensor, personal area network (FA-PAN) when the sensor group is within range of the fixed aggregator module; and
- terminating the MA-PAN when the sensor group is within range of the fixed aggregator module in order to conserve battery power at the mobile aggregator sensor.

* * * * *